Figure 1:

United States Patent [19]

Constantine et al.

[11] Patent Number: 4,996,006

[45] Date of Patent: Feb. 26, 1991

[54] SOLID SHAMPOO COMPOSITION IN COMPACT NEEDLE FORM WITH WATER AS A BINDER

[75] Inventors: Margaret J. Constantine, Poole; Stanislaw Krysztal, Richmond, both of England

[73] Assignee: Constantine & Weir Ltd., Poole, England

[21] Appl. No.: 313,241

[22] Filed: Feb. 21, 1989

[30] Foreign Application Priority Data

Feb. 23, 1988 [GB] United Kingdom ............... 8804138

[51] Int. Cl.$^5$ ....................... C11D 1/12; C11D 1/755
[52] U.S. Cl. .................... 252/550; 252/174; 252/DIG. 13; 252/DIG. 16; 252/90; 252/134
[58] Field of Search ............. 252/DIG. 16, DIG. 13, 252/174, 550

[56] References Cited

U.S. PATENT DOCUMENTS

| | | | |
|---|---|---|---|
| 3,746,647 | 7/1973 | Peloquin | 252/91 |
| 4,012,341 | 3/1977 | Orshitzer et al. | 252/548 |
| 4,320,033 | 3/1982 | Yoshikawa | 252/174 |

FOREIGN PATENT DOCUMENTS

| | | | |
|---|---|---|---|
| 122664 | 5/1984 | European Pat. Off. | |
| 96188 | 5/1972 | France | 252/DIG. 13 |
| 3248899 | 10/1988 | Japan | 252/121 |

OTHER PUBLICATIONS

Chemical Abstracts, vol. 92, No. 18, p. 390, Abstract No. 152886f.

*Primary Examiner*—Paul Lieberman
*Assistant Examiner*—James M. Silbermann
*Attorney, Agent, or Firm*—Cohen, Pontani & Lieberman

[57] ABSTRACT

A solid bar comprising 70% to 90% detergent, preferably sodium lauryl sulphate, in solid needle form and 1% to 10% water, and optionally small amounts of various other ingredients such as conditioners, essential oils, perfumes and dyes, and additional binding agents for the needles. The water, and such other small quantity ingredients as may be required are mixed together and then mixed with the needles, so as to coat them. Predetermined quantities of the coated needles are compacted in a mould under pressure.

10 Claims, 2 Drawing Sheets

SOLID SHAMPOO COMPOSITION IN COMPACT NEEDLE FORM WITH WATER AS A BINDER

This invention relates to shampoos.

Shampoo is usually made from liquid detergent and water with other ingredients such as gelling agents, cream or lotion, perfume, dye and preservatives being added as required.

The process of making shampoo essentially comprises mixing the selected detergent in water to form a homogeneous liquid, after which the dye, perfume and preservative may be added.

A main object of the present invention is to provide an improved form of shampoo having advantages over the liquids or semi-liquids hitherto in general use.

The invention comproises shampoo in the form of a solid bar comprising 70% to 90% detergent in solid needle form and 1% to 10% water. Preferably the detergent is a cationic surfactant such as sodium lauryl sulphate. Small amounts of various other ingredients can be included such as conditioners, essential oils perfumes and dyes, and additional binding agents for the needles.

The invention includes a method of making a solid shampoo bar comprising the steps of mixing 70% to 90% detergent in solid needle form with 1% to 10% water, and such other ingredients as may be required, so as to coat the needles, and compacting predetermined quantitaies of the coated needles in a mould under pressure. For a small bar, the needles can be compacted at room temperature and 40-60 p.s.i. In the finished bar, the needles are apparent, on the surface and throughout the thickness of the bar, and there may be some internal voids.

One composition, designated A, will now be given by way of example, using sodium lauryl sulphate as the main ingredient. This can be conveniently purchased under the trade mark EMPICOL (Albright & wilson) which comes in various grades, EMPICOL LXV being chosen for this example.

The Composition A is as follows:

| | |
|---|---|
| EMPICOL LXV (Sodium Lauryl Sulphate) | 92.0% |
| EMPILAN CDE Fatty Acid Dialkylolamides | 2.0% (a hair conditioner) |
| Water | 3.0% |
| POLYMER JR400 (Union Carbide) (Union Carbide) Polyquaternium 10 | 2.0% (a hair conditioner) |
| D-Panthanol (Roche Chemical Division Hoffman La Roche) | 0.3% (a hair conditioner) |
| 1% Solution in water, U.S. Food, Drugs & Cosmetics Yellow No 5 | 0.2% |
| Perfume | 0.5% |

EMPICOL LXV is in needle form with the composition:

| | |
|---|---|
| Sodium Lauryl Sulphate | 85.0% |
| Unsulphated Matter | 1.5% |
| Sodium Sulphate | 1.6% |
| Sodium Chloride | 1.0% |

Other suitable grades are EMPICOL LMV/T and EMPICOL LZX, in which the proportion of sodium lauryl sulphate in EMPICOL is 89% and 85% respectively.

Four further examples follow:

| | Examples | | | |
|---|---|---|---|---|
| | 1 | 2 | 3 | 4 |
| EMPICOL LXV (Sodium Lauryl Sulphate) | 90.00 | 95.25 | 92.00 | 89.00 |
| Water | 5.00 | 2.00 | 5.00 | (see below) |
| Propylene Glycol (Binding Agent) | | 1.25 | | 2.00 |
| Almond Oil | 2.00 | | 2.00 | |
| Ground Almond | 2.00 | | | |
| Dead Sea Salt | | 1.00 | | |
| Egg Powder | | | | 1.00 |
| Lemon Juice (providing required water) | | | | 2.00 |
| Lemon Peel Powder | | | | 5.00 |
| Crocin (dye) | 0.50 | | | 0.50 |
| Chlorophyllin (dye) | | 0.3 | | |
| Perfume | 0.50 | 0.20 | 1.00 | 0.50 |

As will be understood from the foregoing, the active ingredient sodium lauryl sulphate forms only 85% of EMPICOL LXV. In Example 1, therefore, the percentage of sodium lauryl sulphate is $0.85 \times 90 = 76.5\%$.

In each Example, bars may be made by first mixing the liquids and small quantity ingredients, and then pouring these on to the needles in a planetary mixer. When the needles are coated, which takes little time, predetermined quantities (e.g. 115 gm) are compressed into bars at room temperature and 40-60 p.s.i. Preferably the bars are compacted into the eventual packaging, for example foil. They may be circular (2½ inches in diameter) in plan and oval in vertical section.

Vegetable oils such as henna extract, coconut oil or cocamide (ethanolamines of coconut oil) can be used: various alternative conditioners are available, as used in conventional shampoos. Essential oils can also be added. The water acts as a binder, and as in Examples 2 and 4, a glycol, here propylene glycol, can be added as an additional binding agent.

Figure 2:
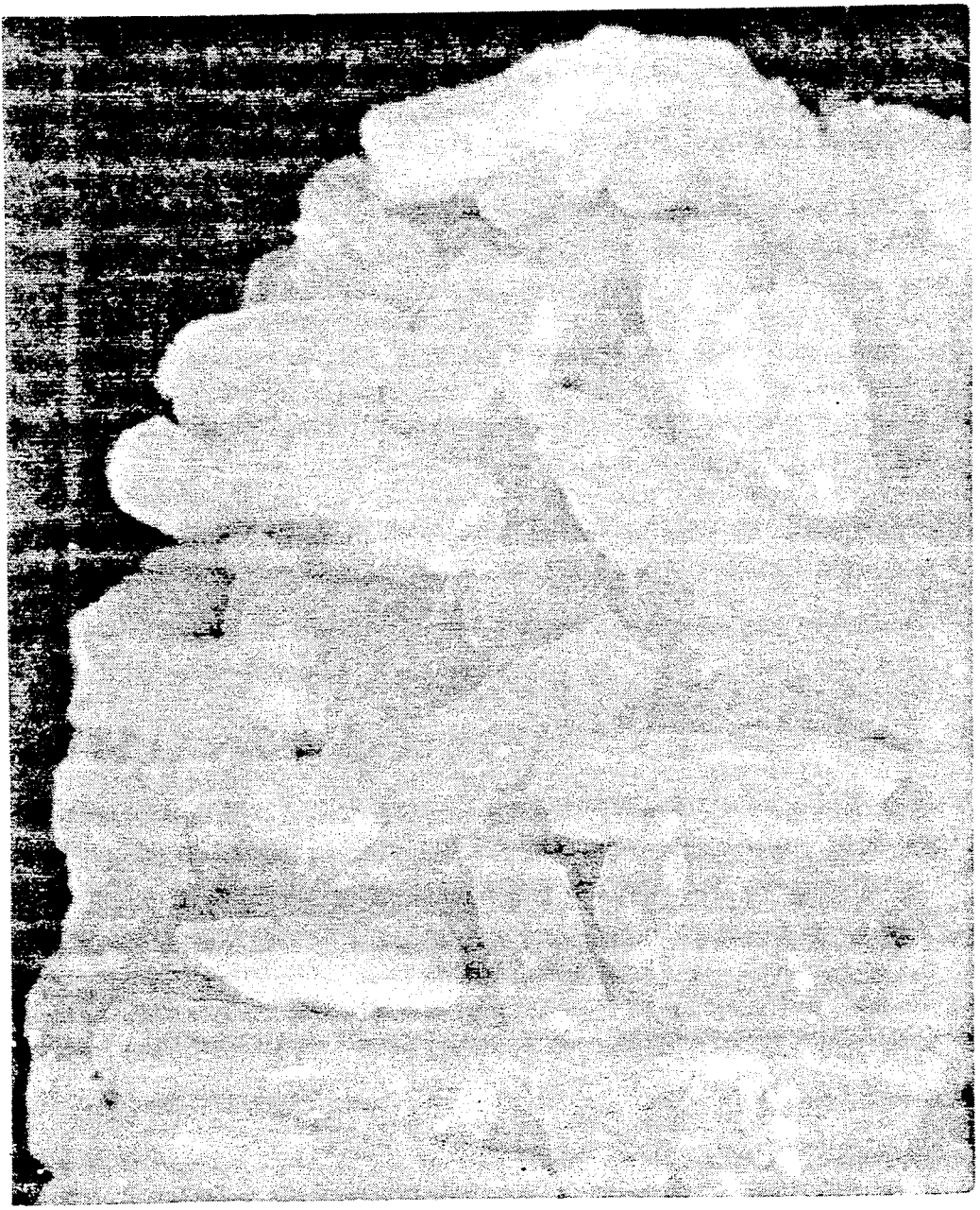

In the accompanying drawings,

FIG. 1 is a photograph of part of the outer surface of a solid detergent bar according to example 3 above, magnified about 6 times; and FIG. 2 is a photograph of a bar broken apart to show the interior, magnified about 12 times.

As will be seen from the drawings, the needles are clearly visible both in the outside and on the interior.

The advantage of the solid shampoo composition of the present invention, over the usual liquid shampoos, is that there is no waste during use. Liquid shampoos run through the fingers and drip, whereas the solid shampoo of the present invention is very economical, just one wipe over wetted hair being sufficeient to provide a substantial lather. Tests have shown that a weight of shampoo in bar form gives more hair washes than the equivalent liquid, in normal use. Furthermore the distinctive appearance and texture of the shampoo tablet makes it readily recognisable and clearly distinguishable from a normal tablet of soap.

We Claim:

1. A solid shampoo bar (comprising) consisting essentially of 70% to 90% detergent in the form of compacted solid needles and 1% to 10% water as a binder, the structure of the bar having the form of compacted needles.

2. A shampoo as in Claim 1 wherein the detergent is sodium lauryl sulphate.

3. A shampoo as in Claim 2, additionally including a conditioner, an essential oil, a perfume or a dye.

4. A shampoo as claimed in claim 2, additionally including 0-5% of a hair conditioner, and 0 to 1% of a perfume and a dye.

5. A shampoo bar consisting essentially of 75% to 80% sodium lauryl sulphate in the form of compacted solid needles compressed with 2% to 5% water as a binder the structure of the bar having the form of compacted needles.

6. A shampoo bar as claimed in claim 5, including an additional binder comprising 1% to 2% glycol.

7. A shampoo bar as claimed in claim 5, additionally comprising a binder, an essential oil, a perfume or a dye.

8. A method of making a solid shampoo bar comprising the steps of mixing 70% to 90% detergent in dry solid needle form with 1% to 10% water as a binder, and at least one further ingredient selected from the group consisting of a hair conditioner, a perfume and a dye so as to coat the needles, and compacting predetermined quantities of the coated needles in a mold under low pressure to form a coherent bar the structure of which has the form of compacted needles.

9. A method as in claim 8 wherein the needles are compacted at room temperature and 40-60 p.s.i.

10. A method of making a solid shampoo bar comprising the steps of:
   (a) mixing 2-5% water with at least one of: additional binder, essential oil, perfume, and dye;
   (b) mixing the liquid from step (a) in a planetary mixer with 75-80% sodium lauryl sulphate in dry needle form having a diameter of approxiamately 1.3 mm to coat the needles; and
   (c) compacting predetermined quantities of the needles in a mold under light pressure so as to form a coherent bar the structure of which has the form of compacted needles.

* * * * *